United States Patent
Koh et al.

(10) Patent No.: US 6,482,445 B1
(45) Date of Patent: Nov. 19, 2002

(54) PROCESS FOR PREPARING STABILIZED LIQUID SILICATE CARBONATE ANTISEPTIC AGENTS

(75) Inventors: Ho Jong Koh, Seoul (KR); Suk Young Lee, Suwon (KR)

(73) Assignee: Nel Biotech Co., Ltd., Kyonggi-Do (KR)

( * ) Notice: Subject to any disclaimer, the term of this patent is extended or adjusted under 35 U.S.C. 154(b) by 0 days.

(21) Appl. No.: 10/072,141

(22) Filed: Feb. 7, 2002

(30) Foreign Application Priority Data

Mar. 29, 2001 (KR) ............................ 01-16507

(51) Int. Cl.$^7$ .................... A61K 33/00; A01N 59/00
(52) U.S. Cl. ...................... 424/715; 424/724
(58) Field of Search .................. 424/715, 724

(56) References Cited

U.S. PATENT DOCUMENTS

| | | | | |
|---|---|---|---|---|
| 4,282,129 A | * | 8/1981 | Blount ................. | 260/29.2 E |
| 4,376,178 A | * | 3/1983 | Blount ................. | 524/47 |
| 5,234,506 A | * | 8/1993 | Winston et al. ....... | 134/40 |
| 5,264,046 A | * | 11/1993 | Winston et al. ....... | 134/42 |
| 5,264,047 A | * | 11/1993 | Winston et al. ....... | 134/42 |
| 5,393,448 A | * | 2/1995 | Winston et al. ....... | 252/109 |
| 5,431,847 A | * | 7/1995 | Winston et al. ....... | 252/174.24 |
| RE35,045 E | * | 10/1995 | Winston et al. ....... | 134/40 |
| 5,464,533 A | * | 11/1995 | Winston et al. ....... | 252/108 |

* cited by examiner

Primary Examiner—Shep K. Rose
(74) Attorney, Agent, or Firm—Ladas & Parry

(57) ABSTRACT

The present invention relates to a process for preparing a liquid silicate carbonate antiseptic agent. According to the present invention, the liquid silicate carbonate antiseptic agent is prepared by the process which comprises a step of dissolving 80–120 g of a silicate in 1 l of purified hot water at 70–90° C. until the silicate is completely ionized; a step of homogeneously emulsifying the mixture by adding 8–15 g of a emulsifier; and a step of stabilizing the resulting mixture by adding sodium carbonate ($Na_2CO_3$) and potassium carbonate ($K_2CO_3$) as carbonates in an amount of 45–80 g, respectively, and stirring the mixture. The liquid silicate carbonate antiseptic agent according to the present invention is characterized by the fact that in preparing the carbonate in a saturation state with sodium carbonate and potassium carbonate, the saturated carbonate is stabilized in aqueous solution by the addition of an effective amount of silicate and emulsifier and the heat treatment, and it has a broad disinfecting and biocidal effects on viruses, gram-positive bacteria and gram-negative bacteria even at a relatively low carbonate concentration and can maintain a sustained biocidal activity.

5 Claims, No Drawings

PROCESS FOR PREPARING STABILIZED LIQUID SILICATE CARBONATE ANTISEPTIC AGENTS

TECHNICAL FIELD

The present invention relates to a process for preparing a liquid silicate carbonate antiseptic agent. More specifically, the present invention provides a process for preparing a non-toxic liquid carbonate antiseptic agent having an improved functionality and a high concentration, wherein in preparing the carbonate in a saturation state with sodium carbonate and potassium carbonate, the supersaturated carbonate is stabilized in aqueous solution by the addition of an effective amount of silicate and emulsifier and the heat treatment.

BACKGROUND ART

Sodium hydroxide generally used as an alkaline antiseptic agent in the prior art has a strong corrosive property and has been suggested being used at the concentration as high as 2% in order to exhibit effective antiseptic effect. However, according to Material Safety Data Sheets (MSDS), it has been described that sodium hydroxide may cause irritation upon exposure to skin and eye and must be carefully handled at all times because it is a toxic chemicals. Further, sodium hydroxide has a little effect for combating viruses such as causative virus of foot-and-mouth disease belonging to international infectious veterinary diseases. Thus, sodium hydroxide has been generally used for disinfecting containers, pens and footholds.

In addition, sodium carbonate which is inexpensive and can be more safely used among alkaline agents has been suggested being used in the form of sodium carbonate solution having a concentration of 4% or more. It is a relatively high concentration.

DISCLOSURE OF THE INVENTION

Thus, the present inventor has studied and experimented for a long period, and then developed a certain liquid silicate carbonate antiseptic agent which has a broad antiseptic and biocidal effects on viruses, gram-positive bacteria and gram-negative bacteria even at a relatively low carbonate concentration and can maintain a sustained biocidal activity.

The object of the present invention is to provide a process for preparing a liquid silicate carbonate antiseptic agent.

More specifically, the object of the present invention is to provide a process for preparing a liquid silicate carbonate antiseptic agent, which comprises a step of dissolving 80–120 g of a silicate in 1 l of purified hot water at 70–90° C. until the silicate is completely ionized; a step of homogeneously emulsifying the mixture by adding 8–15 g of an emulsifier; and a step of stabilizing the resulting mixture by adding sodium carbonate ($Na_2CO_3$) and potassium carbonate ($K_2CO_3$) as carbonates in an amount of 45–80 g, respectively, and stirring the mixture.

BEST MODE FOR CARRYING OUT THE INVENTION

The process for preparing liquid silicate carbonate antiseptic agent according to the present invention comprises a step of dissolving 80–120 g of a silicate in 1 l of purified hot water maintained at 70–90° C. until the silicate is completely ionized; a step of homogeneously emulsifying the mixture by adding 8–15 g of an emulsifier; and a step of stabilizing the resulting mixture by adding sodium carbonate ($Na_2CO_3$) and potassium carbonate ($K_2CO_3$) as carbonates in an amount of 45–80 g, respectively, and stirring the mixture.

As the silicate in the present invention, one or more selected from the group consisting of silicon dioxide ($SiO_2$), sodium silicate ($Na_2SiO_3$) and potassium silicate ($K_2SiO_3$) can be used. It is preferred that the silicate is used in the range of 80 to 120 g with respect to 1 l of purified water. If the silicate is used in an amount not more than 80 g, it is difficult to continuously stabilize the liquid solution. On the other hand, if the silicate is used in an amount greater than 120 g, the antiseptic effect is lowered.

As the emulsifier, one or more selected from the group consisting of propylene glycol (PG), polyethylene glycol and glycerol can be used. It is preferred that the emulsifier is used in the range of 8 to 15 g with respect to 1 l of purified water. If the emulsifier is used in an amount not more than 8 g, it is difficult to continuously stabilize the liquid solution. On the other hand, if the silicate is used in an amount greater than 15 g, the antiseptic effect is lowered.

As the silicate, one or more selected from the group consisting of silicon dioxide ($SiO_2$), sodium silicate ($Na_2SiO_3$) and potassium silicate ($K_2SiO_3$) can be used.

As the carbonate, it is preferred that both of sodium carbonate and potassium carbonate are simultaneously used, preferably at the same concentration. The respective carbonates are preferably used in an amount in the range of 45 to 80 g with respect to 1 l of purified water.

Preferably, in order to improve a pleasant flavor of the antiseptic product a composite flavoring agent formed by dissolving flavoring agents in ethyl benzoate and then mixing them together, and a naphthal coloring matter can further be incorporated into the product. The reason why the coloring matter is added is to readily differentiate the product to which the silicate carbonate antiseptic agent is added, from other products.

The antiseptic agent prepared according to the present invention can be used for disinfecting, for example, farm floor, farm indoor, drinking utilities, farm outdoor, vehicles and disinfecting vessels, etc. in the form of 100 to 5,000-fold dilutions, preferably 150 to 1,500-fold dilutions, depending on the site at which the antiseptic agent of the present invention is practically used.

The present invention will be more specifically illustrated through the following examples. A person having an ordinary knowledge in this technical field would clearly understand that these examples are intended only to specifically explain the present invention and the scope of the present invention is not limited by these examples in any manner.

EXAMPLE

Preparation of Liquid Carbonate Antiseptic Agent 100 g of sodium silicate was added to 1 l of purified hot water maintained at 80° C. and then dissolved therein with thorough mechanical stirring so that silicate is completely ionized. 10 g of glycerol was added thereto to emulsify the mixture. Then, sodium carbonate ($Na_2CO_3$) and potassium carbonate ($K_2CO_3$) were added in an amount of 60 g, respectively, and the resulting mixture was stirred to obtain the antiseptic agent stabilized in aqueous solution.

Test 1: Viricidal Activity Against Foot-and-mouth Virus

The viricidal activity of the liquid carbonate antiseptic agent as prepared in the above Example 1 according to the present invention was examined using FMDV O type virus as foot-and-mouth disease virus.
1) Viruses
   FMDV O type virus [wild-type viral strain isolated by Kasetsart University of Thailand]
2) Cell Lines
   BHK-21 cell line (baby hamster kidney cell line) which is incubated on α-DMEM medium (Gibco-BRL USA) and is sensitive to foot-and-mouth virus
3) Test Method
   The titer against foot-and-mouth virus as the test strain was measured by inoculating 10-fold serial dilutions of BHK-21 cell line onto 96 well plate, daily monitoring the plate and then finally reading the plate at the point of 96 hours. The titer thus measured was subjected to the test for viricidal effect of the antiseptic agent according to the present invention to conduct the present test.
   To measure the viricidal effect of the liquid silicate carbonate antiseptic agent according to the present invention BHK-21 cell line was incubated on 96 well plate in $CO_2$ incubator at 37° C. to form a monolayer, and the antiseptic agent and 10-fold serial dilutions of foot-and-mouth disease virus were reacted in the ratio of 1:1 and then inoculated onto the cell. The cytotoxicity (CPE) appearing on the cells to which the antiseptic-treated virus is inoculated was finally read to determine the presence or absence of inactivation of the test virus.
4) Inspection of the Test Method
   The viral titer against FMDV O type foot-and-mouth disease virus used in the present test against BHK-21 cell line was measured to be $10^{7.325}$ $TCID_{50}$/ml, which is the level sufficient for measuring the viricidal activity. Further, since the antiseptic agent used in the test can exhibit cytotoxic activity, which can influence upon the reading of viricidal acitivity, the cytotoxicity of the antiseptic agent was determined. As a result, it could be identified that since the cytotoxicity of 2-fold dilution of the antiseptic agent is below 3,200 times, there is no problem in reading the test result when the test is conducted using the virus at the level of $10^{7.325}$ $TCID_{50}$/ml.
5) Result of the Test
   As the result of the test wherein the antiseptic agent according to the present invention is applied to FMDV O type foot-and-mouth disease virus, it could be observed that the antiseptic agent of the present invention exhibit a superior viricidal effect at the level of 50 to 170-fold dilutions without any degenerative effect on the cell, and further exhibits the disinfecting effect of attenuating the viral activity due to protein degeneration at the level of 180 to 200-fold dilutions, as can be seen from the following Table 1.

TABLE 1

Viricidal activity against FMDV O type foot-and-mouth virus (unit: log(virus titer))

| Dilution factor | 50 | 100 | 150 | 170 | 180 | 190 | 200 |
|---|---|---|---|---|---|---|---|
| Control group |  |  |  | 7.325 |  |  |  |
| Test group | 0 | 0 | 0 | 0 | 4.6 | 4.8 | 4.8 |

Test 2: Viricidal Activity in Poultry

To further examine the viricidal activity of the antiseptic agent of the present invention the test was conducted to measure the viricidal activity against Newcastle disease virus and Avian influenza virus.

1) Viruses
   Newcastle disease virus (NDV), isolated from the state of La Sota
   Avian influenza virus (AIV), isolated from Korea
2) SPF Line Breeding Egg
   10-days aged SPF line breeding egg
3) Test Method
   Newcastle disease virus and Avian influenza virus were inoculated onto 10-days aged SPF line breeding eggs and then the titer against viruses thus prepared was calculated from the hemagglutination reaction. Then, the viricidal activity of the antiseptic agent of the present invention was examined using 100 HA unit of viruses.
4) Inspection of the Test Method
   Since the antiseptic agent used in the test can exhibit cytotoxic activity, which can influence upon the reading of viricidal acitivity, the cytotoxicity of the antiseptic agent was determined. As a result, it could be identified that since the cytotoxicity of 2-fold dilution of the antiseptic agent is below 3,200 times, there is no problem in reading the test result when the test is conducted using the virus at the level of $10^{7.325}$ $TCID_{50}$/ml.
5) Result of the Test
   The test viruses were inoculated onto SPF line breeding eggs to prepare the seed toxin, which was used in the hemagglutination reaction to calculate the titer against viruses, and then the obtained titer was adjusted to 100 HA unit and then used to measure the viricidal activity of the antiseptic agent. As the result, it could be identified that the antiseptic agent of the present invention exhibits viricidal activity against both viruses at the level of 150-fold dilution as can be seen from the following Table 2. From this result, it can be estimated that the antiseptic agent of the present invention exhibits a superior viricidal activity against such two kinds of viruses, which are currently at issue in the world.

TABLE 2

Viricidal activity of the antiseptic agent of the present invention against Newcastle disease virus (NDV) and avian influenza virus (AIV)

| Test virus | NDV | AIV |
|---|---|---|
| Control group | 512 | 256 |
| Test group | −ve [~150] | −ve [~150] |

Note)
The numerical values denote the dilution factor and the expression "−ve [~150]" means that no inhibitory effect on hemoglobin is present at the level of 150-fold dilution.

Test 3: Bactericidal Activity Against Pathogenic Bacteria

The test was conducted to identify the bactericidal activity of the antiseptic agent according to the present invention.
1) Test Strains
   *Salmonella typhimurium* (available from Jeonbuk University of Korea)
   *Salmonella enteritidis* (available from Jeonbuk University of Korea)
   *Staphylococcus bronchiseptica* (available from Jeonbuk University of Korea)
   *Staphylococcus aureus* (available from Keonkook University of Korea)
   *Escherichia coli* 0157:H7 (available from Jeonbuk University of Korea)
2) Test Method
   Preparation of bacterial solution: The test strains were inoculated onto Brain infusion broth and incubated with shaking at 37° C. for 24 to 48 hours to maintain the activity of the strains. Only the bacterial strains were resuspended in sterilized physiological saline buffer to adjust to $1\times10^8$/ml. The bacterial solution thus adjusted was diluted with 10-fold serial dilution to finally prepare the bacterial solution at the concentration of $1\times10^4$/ml.

Preparation of the antiseptic agent: The antiseptic agent for the test group was prepared by diluting the antiseptic agent prepared in Example 1 with sterilized physiological saline buffer to the optimal dilution factor.

Method: For the test group, the antiseptic agent diluted at respective concentrations was mixed with the same amount of the bacterial solution. In case of the control group, physiological saline buffer was used instead of the antiseptic agent. The mixture was allowed to stand at room temperature for 10 minutes, plated on Brain Heart Infusion agar and then incubated to count the number of colonies.

3) Inspection of the Test Method

The significance of the test result was confirmed by conducting the test using respective bacteria at the concentrations of $5\times10^2$ colonies and $1\times10^3$ colonies, respectively, at the time of inoculation. It was confirmed that the result is significant by repeatedly conducting the same test three times or more.

4) Result of the Test

The test group was treated using the antiseptic agent according to the present invention on the basis of the test method as described above, and then the concentration at which no bacterial colony is formed was considered as the bactericidal concentration. The medium not occurring the bacterial colonies was incubated for further 24 hours to reconfirm whether the colony is formed or not.

processed test specimen pretreated with the liquid antiseptic agent obtained from Example 1 according to the present invention was placed in the center area of agar medium, and then 0.2 ml of the bacterial suspension obtained above was uniformly inoculated on the test specimen and stationary incubated at 37° C. for 18 hours to count the number of bacterial colonies thus formed. The variation from the control specimen was calculated using the following equation:

$$\text{Variation} = \log(B/A) - \log(C/A)$$

In the above equation, A denotes the bacterial number immediately after inoculation on untreated specimen; B denotes the bacterial number after 18 hours incubation on untreated specimen; and C denotes the bacterial number after 18 hours incubation on treated specimen.

Note)
1. In the test, only the data in case of $\log(A/B)>2$ is regarded as the effective test data.
2. The antibacterial effects against microorganisms are compared with each other on the basis of the decreasing rate of bacterial number.

$$\text{Decreasing rate } \% = (B-A)/B \times 100$$

In the above equation, A denotes the bacterial number on the test specimen incubated for a certain contacting period after inoculation; and B denotes the bacterial number on the test specimen taken immediately after inoculation.

5) Test Result

In order to identify the disinfecting effect, i.e. the duration and maintenance of the antibacterial activity, of the present invention using the microorganism belonging to Staphylococci, *Staphylococcus aureus,* as the test microorganism, the antiseptic agent according to the present

TABLE 3

Maximal dilution factor at which 100% bactericidal activity is exhibited against repective bacteria

| Kinds of bacteria | *Salmonella typhimurium* | *Salmonella enteritidis* | *Bordetella bronchieseptica* | *Staphylococcus aureus* | *E. coli* 0157:H7 |
|---|---|---|---|---|---|
| Test group | 1,500 | 1,500 | 1,500 | 100 | 1,000 |

Test 4: Test for Maintenance of Antibacterial Activity

The antiseptic agent of the present invention has a sustained bactericidal activity as well as a superior bactericidal activity. Thus, in order to identify how long the bactericidal activity of the antiseptic agent according to the present invention is sustained, the effect of the present invention was identified using the clothes material as the test subject to be sterilized and disinfected by spreading the antiseptic agent for the test group on the test subject and then determining the duration of its bactericidal activity.

1) Test strain: *Staphylococcus aureus*
2) Application method: Applied to the clothes material by spray-treating with the antiseptic agent
3) Test specimen: Clothes material specimen in the form of 18×18 mm square
4) Test method: Bioassay method (KS K 0693 certified method)

The bacterial number of the test bacterial solution was adjusted to $10-24\times10^4$/ml by 10-fold serial dilution. The invention as prepared in Example 1 was 120-fold diluted so that the initial antibacterial subjected to the test.

From the following Table 4, it can be seen that the initial antibacterial activity of the 120-fold dilution of the antiseptic agent was 99.9% and even after 10 washes the antibacterial activity was maintained at the level as high as 99.2%.

TABLE 4

Test for maintenance of antibacterial activity

| Staphylococcus aureus (bacterial decreasing rate: %) | | | |
|---|---|---|---|
| Washing number | 0 | 10 | 20 |
| Antibacterial activity (%) | 99.9 | 99.2 | 94.6 |

The liquid silicate carbonate antiseptic agent according to the present invention is characterized by the fact that in preparing the carbonate in a saturation state with sodium carbonate and potassium carbonate, the supersaturated carbonate is stabilized in aqueous solution by the addition of an effective amount of silicate and emulsifier and the heat treatment, and it has a broad disinfecting and biocidal effects on viruses, gram-positive bacteria and gram-negative bacteria even at a relatively low carbonate concentration and can maintain a sustained biocidal activity.

What is claimed is:

1. A process for preparing a liquid silicate carbonate antiseptic agent characterized in that it comprises a step of dissolving 80–120 g of a silicate in 1 l of purified hot water at 70–90° C. until the silicate is completely ionized; a step of homogeneously emulsifying the mixture by adding 8–15 g of an emulsifier; and a step of stabilizing the resulting mixture by adding sodium carbonate ($Na_2CO_3$) and potassium carbonate ($K_2CO_3$) as carbonates in an amount of 45–80 g, respectively, and stirring the mixture.

2. The process according to claim 1 characterized in that the silicate is one or more selected from the group consisting of silicon dioxide ($SiO_2$), sodium silicate ($Na_2SiO_3$) and potassium silicate ($K_2SiO_3$).

3. The process according to claim 1 characterized in that the emulsifier is one or more selected from the group consisting of propylene glycol (PG), polyethylene glycol and glycerol.

4. The process according to claim 1 characterized in that sodium carbonate and potassium carbonate are simultaneously used.

5. The process according to claim 1 characterized in that sodium carbonate and potassium carbonate are used respectively in the range of 45 to 80 g with respect to 1 l of purified water.

* * * * *